United States Patent [19]
Hurlimann et al.

[11] Patent Number: 6,133,735
[45] Date of Patent: Oct. 17, 2000

[54] MAGNETIC RESONANCE LOGGING METHOD AND APPARATUS

[75] Inventors: Martin D. Hurlimann; Yi-Quao Song; Seungoh Ryu; Pabitra N. Sen, all of Ridgefield, Conn.

[73] Assignee: Schlumberger Technology Corporation, Ridgefield, Conn.

[21] Appl. No.: 09/198,535

[22] Filed: Nov. 24, 1998

Related U.S. Application Data

[63] Continuation-in-part of application No. 08/936,892, Sep. 25, 1997, abandoned.

[51] Int. Cl.$^7$ .................................................. G01V 3/00
[52] U.S. Cl. ............................................. 324/303; 324/300
[58] Field of Search ................................. 324/303, 306, 324/307, 309, 300

[56] References Cited

U.S. PATENT DOCUMENTS

| | | | |
|---|---|---|---|
| 3,667,035 | 5/1972 | Slichter | 324/303 |
| 3,723,856 | 3/1973 | Brown | 324/303 |
| 4,035,718 | 7/1977 | Chandler . | |
| 4,528,508 | 7/1985 | Vail, III . | |
| 4,656,422 | 4/1987 | Vail, III et al. . | |
| 4,710,713 | 12/1987 | Strikman | 324/303 |
| 4,717,878 | 1/1988 | Taicher et al. . | |
| 4,724,385 | 2/1988 | Vail, III . | |
| 4,804,918 | 2/1989 | Vail, III . | |
| 5,055,787 | 10/1991 | Kleinberg et al. . | |
| 5,055,788 | 10/1991 | Kleinberg et al. | 324/303 |
| 5,278,501 | 1/1994 | Guilfoyle | 324/303 |
| 5,363,041 | 11/1994 | Sezginer . | |
| 5,428,291 | 6/1995 | Thomann et al. . | |
| 5,596,274 | 1/1997 | Sezginer . | |

FOREIGN PATENT DOCUMENTS

| | | |
|---|---|---|
| PCT/EP96/ 0291 | 6/1996 | WIPO . |
| PCT/US96/ 15301 | 9/1996 | WIPO . |

OTHER PUBLICATIONS

O.A. Trushkin, O.A. Shushnakov, & A.V. Legchenko, "Surface NMR Applied to an Electronconductive Medium", Geophysical Prospecting, 1995, 43, 623–633.

O.A. Shushnakov, "Surface NMR Measurement of Proton Relaxation Times in Medium to Coarse–Grained Sand Aquifier", 1996, Magnetic Resonance Imaging, vol. 14, Nos. 7/8 pp. 959–960.

R.C. Merrick, S.H. Coutruie, & D.L. Best, "An Improved Nuclear Magnetism Logging System and Its Application to Formation Evaluation", Sep. 23–26, 1979, Las Vegas, Nevada, SPE8361.

S.C. Bushong, ScD, "Magnetic Resonance Imaging Physical and Biological Principles", Houston, Texas, pp. 279–297.

Bagguley, D.M.S., "Pulsed Magnetic Resonance: NMR, ESR, And Optics A Recognition Of E.L. Hahn", 1992, pp. 317–345.

Melton and Pollak, JMRA 122, pp. 42–49, 1996.

Solomon, Phys. Rev. Lett. 2, pp. 301–302, 1952.

(List continued on next page.)

*Primary Examiner*—Louis Arana
*Attorney, Agent, or Firm*—William B. Batzer; Martin M. Novack

[57] ABSTRACT

A technique is provided for determining a nuclear magnetic resonance characteristic of formations surrounding an earth borehole, including the following steps: providing a logging device that is moveable through the borehole; providing, on the logging device, first and second coils having respective axes that are generally orthogonal; producing, at the logging device, a prepolarizing signal; applying pulse sequence signals to the first and second coils, the pulse sequence signals implementing repeated refocusing of spins in the formations by both adiabatic and non-adiabatic reorienting of the spins to form spin echoes; and detecting, at the logging device, the spin echoes from the formations, the spin echoes being indicative of the nuclear magnetic resonance characteristic of the formations.

39 Claims, 9 Drawing Sheets

OTHER PUBLICATIONS

E.J. Wells And K.H. Abramson, JMR, 1, pp. 378–392, 1969.

Hwang, VanZijil and Garwood, JMR, 133, pp. 200–203, 1998.

Garwood and Ugurbill, "$B_1$ Insensitive Adiabatic RF Pulses" in "NMR Basic Principles and Progress", M. Ruin and J. Seelig, Eds., pp. 109–144, Springer–Verlag, N.Y., 1992.

A. Tannus and M. Garwood, JMR A 120, pp. 133–137, 1996.

E. Kupce and R. Freeman JMR A 118, pp. 299–303, 1996.

T.L. Hwang and A.J. Shaka, JMR A 112, pp. 275–279, 1995.

M.H. Levitt and R. Freeman JMR 43, 65–80, 1981.

V. Ermakov, J. Bohlen, G. Bodenhausen, JMR A 103, pp. 226–229 1993.

S. Connolly, D. Nishimura, A. Macovski JMR 83, pp. 324–334, 1989.

M. Garwood and Y. Ke, J. Mag. Res., 94, pp. 511–525, 1991.

T. Hwang, P. Van Ziji and M. Garwood, JMR 124, pp. 250–254, 1997.

R. de Graaf, K. Nicolay, M. Garwood, MRM, 35, pp. 652–657, 1996.

A. Abragam, The Principles Of Nuclear Magnetism, Oxford Univ. Press, 1961 pp. 65–68, 86, Fig. III 5 and III 6.

P. Mansfield, Pulsed Magnetic Resonance, pp. 317–345, 1992.

S. Connolly, G. Glover, D. Nishimura, and A. Macovski, MRM 18, 28, 1991.

Webb, Rev. Sci, Inst., V48, p. 1585, 1978.

Ernst et al., "Principles Of Nuclear Magnetic Resonance In One And Two Dimensions", pp. 91–241, Clarendon Press, 1987.

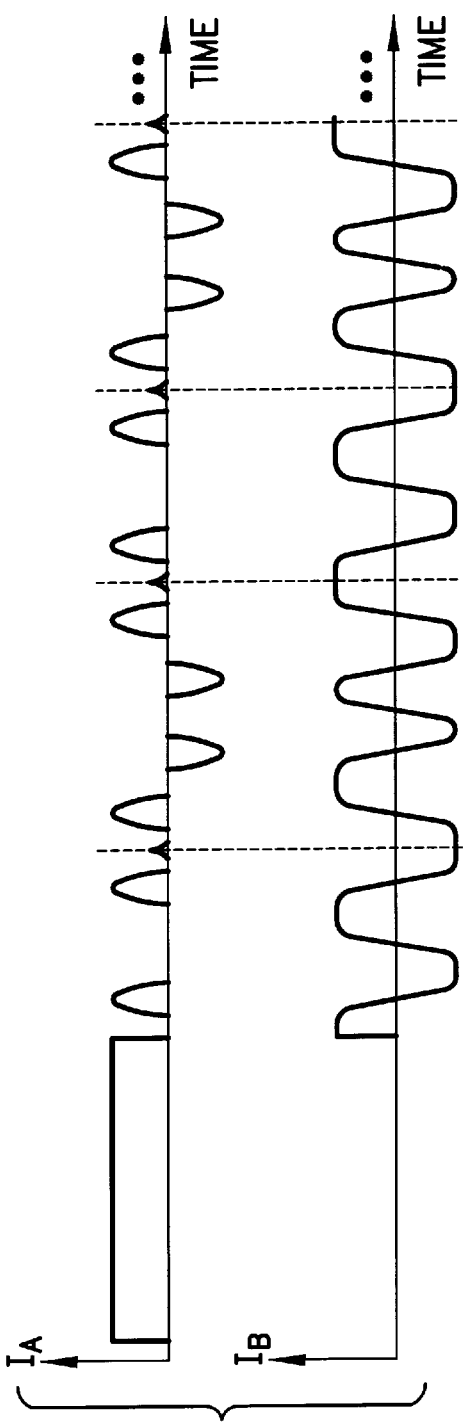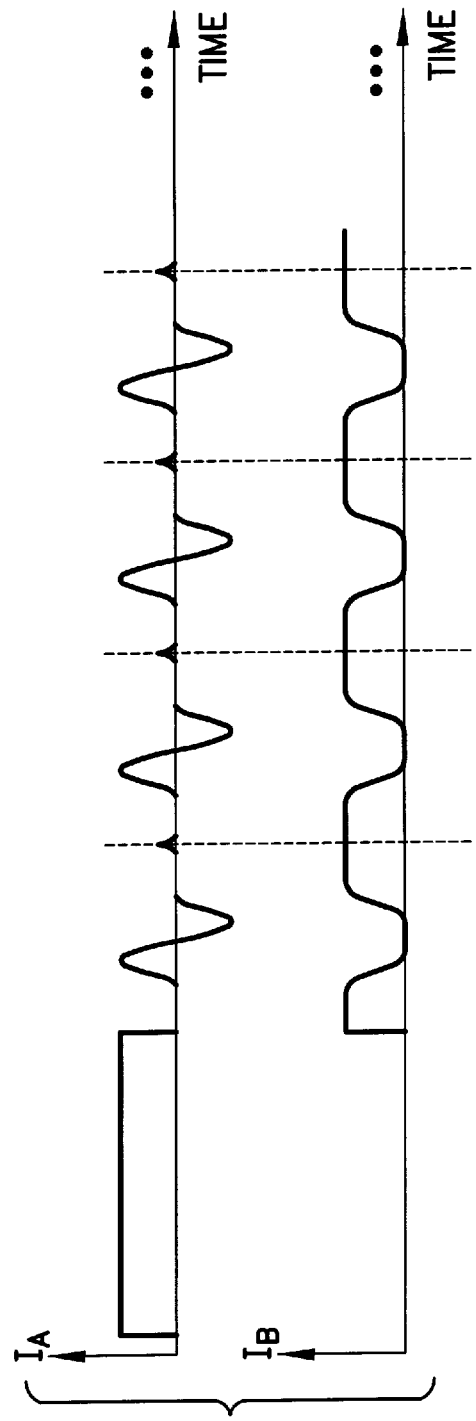

MAGNETIC RESONANCE LOGGING METHOD AND APPARATUS

RELATED APPLICATION

This is a continuation-in-part of U.S. patent application Ser. No. 08/936,892, filed Sep. 25, 1997, now abandoned and assigned to the same assignee as the present Application. The subject matter of the present Application is related generally to the subject matter of U.S. patent application Ser. No. 09/198,715 and the subject matter of U.S. patent application Ser. No. 09/199,019, both filed of even date herewith, and both assigned to the same assignee as the present Application.

FIELD OF THE INVENTION

This invention relates to nuclear magnetic resonance logging, and, more particularly, to a method and apparatus for magnetic resonance logging of an earth borehole to obtain information about properties of formations surrounding the earth borehole.

BACKGROUND OF THE INVENTION

General background of nuclear magnetic resonance (NMR) well logging is set forth, for example, in U.S. Pat. No. 5,023,551. Briefly, in NMR operation the spins of nuclei align themselves along an externally applied static magnetic field. This equilibrium situation can be disturbed by a pulse of an oscillating magnetic field (e.g. an RF pulse), which tips the spins away from the static field direction. After tipping, two things occur simultaneously. First, the spins precess around the static field at the Larmor frequency, given by $\omega_0=\gamma B_0$, where $B_0$ is the strength of the static field and $\gamma$ is the gyromagnetic ratio. Second, the spins return to the equilibrium direction according to a decay time T1, the spin lattice relaxation time. For hydrogen nuclei, $\gamma/2\pi=4258$ Hz/Gauss, so, for example, for a static field of 235 Gauss, the frequency of precession would be 1 MHz. Also associated with the spin of molecular nuclei is a second relaxation, T2, called the spin-spin relaxation time. At the end of a ninety degree tipping pulse, all the spins are pointed in a common direction perpendicular to the static field, and they all precess at the Larmor frequency. However, because of small inhomogeneities in the static field due to imperfect instrumentation or microscopic material heterogeneities, each nuclear spin precesses at a slightly different rate. T2 is a time constant of this "dephasing".

A widely used technique for acquiring NMR data both in the laboratory and in well logging, uses an RF pulse sequence known as the CPMG (Carr-Purcell-Meiboom-Gill) sequence. As is well known, after a wait time that precedes each pulse sequence, a ninety degree pulse causes the spins to start precessing. Then a one hundred eighty degree pulse is applied to keep the spins in the measurement plane, but to cause the spins which are dephasing in the transverse plane to reverse direction and to refocus. By repeatedly reversing the spins using one hundred eighty degree pulses, a series of "spin echoes" appear, and the train of echoes is measured and processed.

Further Background, set forth in the referenced copending parent application Ser. No. 08/936,892, is summarized as follows: The static field may be naturally generated, as in the case for the earth's magnetic field $B_E$. The NML™ nuclear logging tool of Schlumberger measures the free precession of proton nuclear magnetic moments in the earth's magnetic field. See, for example, U.S. Pat. No. 4,035,718. The tool has at least one multi-turn coil wound on a core of non-magnetic material. The coil is coupled to the electronic circuitry of the tool and cooperatively arranged for periodically applying a strong DC polarizing magnetic field, $B_P$, to the formation in order to align proton spins approximately perpendicular to the earth's field, $B_E$. The characteristic time constant for the exponential buildup of this spin polarization is the spin-lattice relaxation time, $T_1$. At the end of polarization, the field is rapidly terminated. Since the spins are unable to follow this sudden change, they are left aligned perpendicular to $B_E$ and therefore precess about the earth's field at the Larmor frequency $f_L=\gamma B_E$. The Larmor frequency in the earth's field varies from approximately 1300 to 2600 Hz, depending on location. The spin precession induces in the coil a sinusoidal signal of frequency $f_L$ whose amplitude is proportional to the number of protons present in the formation. Additives in the borehole fluid are required to prevent the borehole fluid signal from dominating the formation signal. The tool determines the volume of free fluid in the formation.

A further nuclear magnetic resonance approach employs a locally generated static magnetic field, $B_o$, which may be produced by one or more permanent magnets, and RF antennas to excite and detect nuclear magnetic resonance to determine porosity, free fluid ratio, and permeability of a formation. See, for example, U.S. Pat. Nos. 4,717,878 and 5,055,787.

Nuclear magnetic resonance has proven useful in medical applications to perform noninvasive examinations of the interior organs and structures of an organism. See P. Mansfield, Pulsed Magnetic Resonance: NMR, ESR, And Optics, 317–345 (D. M. S. Baugguley ed., Cleardon Press, Oxford, 1992). The desire for faster imaging led to the development of commercial and laboratory NMR imaging systems in the medical field which use various gradient-echo techniques consisting of radio frequency pulses, $\alpha$, in combination with switched magnetic field gradients to generate an image. See Stewart C. Bushong, Magnetic Resonance Imaging: Physical And Biological Principles, 279–286, (2d edition, 1996). Known techniques such as fast low angle shot (FLASH) and fast imaging with steady state precession (FISP) require an RF excitation pulse, $\alpha$, of approximately 90° while other techniques vary the flip angle between 30° and 70° to maximize magnetic resonance strength.

As pointed out in the referenced copending Application, the tools and techniques developed in the prior art have various drawbacks that limit their utility in practical applications. These limitations include a shallow depth of investigation and restrictions on the shape and size of the region of investigation.

SUMMARY OF THE INVENTION

In the referenced copending U.S. patent application Ser. No. 08/936,892 there is disclosed an apparatus and technique for NMR logging that is based on non-resonant excitation and refocusing and exhibits a number of advantageous features: The volume of investigation is large compared with the conventional resonant operation. Also, the signal coming from different depths can be differentiated by its Larmor frequency. The technique thereof utilizes a pair of magnetic field generating sources, preferable orthogonally wound coils, that can be energized with large currents in a controlled manner to produce orthogonal magnetic fields in the formation. With appropriate switching of the currents, the direction of the generated magnetic field in the formation can then be changed abruptly. The rate of change of the direction of the magnetic field in the formation has to be fast compared to the local Larmor frequency. This way, the spins cannot follow the direction of the magnetic field and the spins end up orthogonal to the applied magnetic field. Effectively, it is as though all the spins have undergone a 90° pulse. (In the conventional resonant excitation, only spins where the applied field is within a particular small range are excited. In practise, this leads to relatively thin shells of sensitive regions.) Now, the spins undergo a free induction decay with a Larmor frequency proportional to the local field produced by the presently activated coil. Since the field produced by the coil in the formation is highly non-uniform, there is a large range of Larmor frequencies and the net magnetization will decay very quickly (that is, $T^*_2$ is very short). This dephasing can be reversed by forming an echo which is achieved by reversing the field abruptly after a time t. The sense of rotation for the precessing spins is reversed and an echo is formed at a total time 2t, when the magnetization of all the spins is in phase again. This can then be repeated over and over to obtain a train of echoes. The condition for abrupt field reversal is that the rate of change of direction of the applied field has to be fast compared to the Larmor frequency. For appropriate electromagnetic coils, Larmor frequencies generally in the range of up to 250 kHz can be expected. This would indicate that the reversal should be fast compared to about 4 μs. As described in the referenced copending Application, the condition of extremely fast reversal can be alleviated by first reducing the current in the coil to a lower level. This does not change the direction of the total field appreciably, provided it is large compared to background field. The condition of fast reversal will then be significantly reduced, because now it only has to be fast compared to the lowered Larmor frequency. The abrupt change of current direction can thus be replaced by a sine shaped modulation. A condition is that the zero crossing around values of ± background field occurs fast compared to the Larmor frequency corresponding to the background field. For the earth's magnetic field, the reversal should therefore be fast compared to a fraction of a millisecond.

As will be treated in further detail hereinbelow, a limitation on the just described operation of a pulsed gradient logging technique arises because a background magnetic field (e.g. earth's magnetic field) can cause imperfect refocusing, and very fast decay of the echoes, since it will be adding to the applied magnetic field during part of a pulse cycle and subtracting from the applied magnetic field during another part of the cycle. This disadvantage is addressed and solved by the present invention.

In accordance with an embodiment of the method of the invention, there is provided a technique for determining a nuclear magnetic resonance characteristic of formations surrounding an earth borehole, comprising the following steps: providing a logging device that is moveable through the borehole; providing, on the logging device, first and second coils having respective axes that are generally orthogonal; producing, at said logging device, a prepolarizing signal; applying pulse sequence signals to the first and second coils, the pulse sequence signals implementing repeated refocusing of spins in the formations by both adiabatic and non-adiabatic reorienting of the spins to form spin echoes; and detecting, at the logging device, the spin echoes from the formations, the spin echoes being indicative of said nuclear magnetic resonance characteristic of the formations.

In a preferred embodiment of the invention, the adiabatic reorientations are performed by varying simultaneously the signals in the first and second coils.

The technique of the invention is operative in a setting wherein a background magnetic field (e.g. earth's magnetic field, which is always present in the formations) introduces a spurious phase component to the spins during the indicated non-adiabatic reorientations. The adiabatic reorientations used in the invention are operative to rotate the spins over a range of angles such that the background magnetic field introduces a further phase component to the spins, the further phase component substantially cancelling the spurious phase component.

Further features and advantages of the invention will become more readily apparent from the following detailed description when taken in conjunction with the accompanying drawings.

BRIEF DESCRIPTION OF THE DRAWINGS

FIG. 3, which includes

FIG. 8 illustrates signals that can be applied to the coils A and B to obtain a pulse sequence in accordance with an embodiment of the invention which compensates at every even echo the residual phase shift caused by finite duration of the non-adiabatic field reversal.

FIG. 9 illustrates signals that can be applied to the coils A and B to obtain a pulse sequence in accordance with another embodiment of the invention which compensates at every even echo the residual phase shift caused by finite duration of the non-adiabatic field reversal.

FIG. 10, which includes In FIG. 10A, n=1, corresponding to the pulse sequence in FIG. 9. The diagram of FIG. 10B is for n=3.

DETAILED DESCRIPTION

Figure 1:
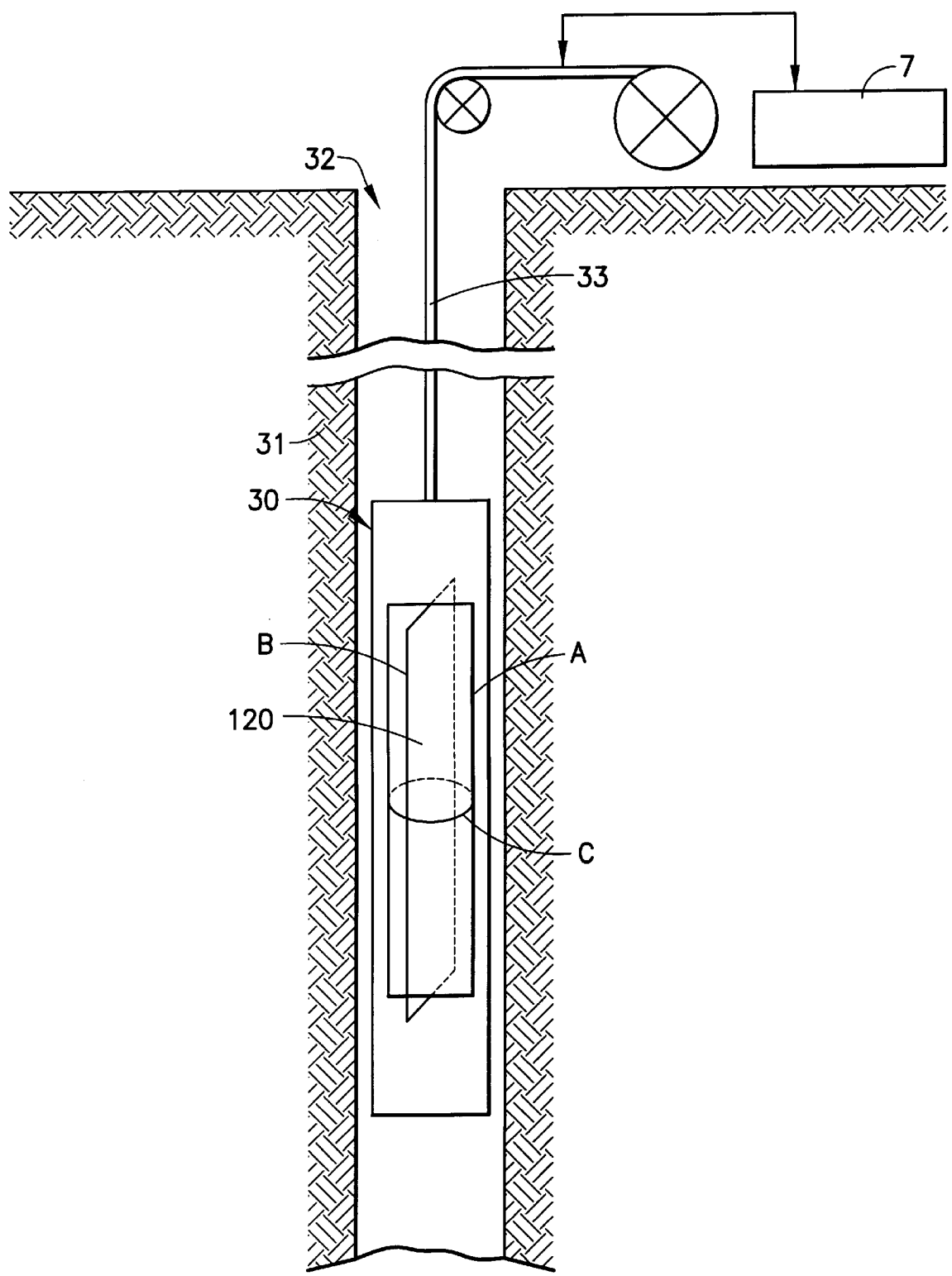
FIG. 1 is a diagram, partially in schematic and partially in block form, that can be used in practicing embodiments of the invention.

Referring to FIG. 1, there is shown an apparatus for investigating subsurface formations 31 traversed by a borehole 32, which is generally of the type described in the referenced copending U.S. patent application Ser. No. 08/936,892 and which, with the features described herein, can be used in practicing embodiments of the present invention. An investigating apparatus or logging device 30 is suspended in the borehole 32 on an armored cable 33, the length of which substantially determines the relative depth of the device 30. The cable length is controlled by suitable means at the surface such as a drum and winch mechanism. Surface equipment, represented at 7, can be of conventional type, and can include a processor subsystem, communicates with the downhole equipment. Although the logging device or tool 30 is shown as a single body, it may alternatively comprise separate components, and the tool may be combinable with other logging tools. Also, while a wireline is illustrated, alternative forms of physical support and communicating link can be used, for example in a measurement while drilling system.

The tool 30 has a pair of coils, respectively designated as coil A and coil B, wound on a non-conductive core 120, which may be, for example, a non-conductive, magnetically permeable core made of a suitable material such as ferrite, laminated permealloy, or tape-wound metglass. A non-conductive, non-magnetically permeable core could also be used. In the embodiment of FIG. 1, the axis of the logging tool (and the core 120) is a longitudinal axis. The coils A and B are wound on axes that are mutually orthogonal, and are both orthogonal to the longitudinal axis. The coils A and B are preferably elongated in the axial direction, with the elongated legs of the conductor loops thereof being parallel to the longitudinal axis of the tool. The angular density of the windings is preferably sinusoidal to insure a two-dimensional dipolar field distribution. The coils A and B are azimuthally offset by 90° to obtain dipolar field characteristics for the coils A and B that are orthogonal in the formation and to minimize mutual inductance of the coils A, B. The coils can be protected by a nonconductive, nonmagnetic, abrasion and impact resistant cover made of a suitable material such as fiberglass, plastic, ceramic, or a composite of these materials. Another coil, designated coil C, which can be used in embodiments of the system described in the referenced copending application Ser. No. 08/936,892, and in embodiments hereof, is wound around the longitudinal axis of the core 120. Thus, all three coils are mutually orthogonal.

Figure 2:
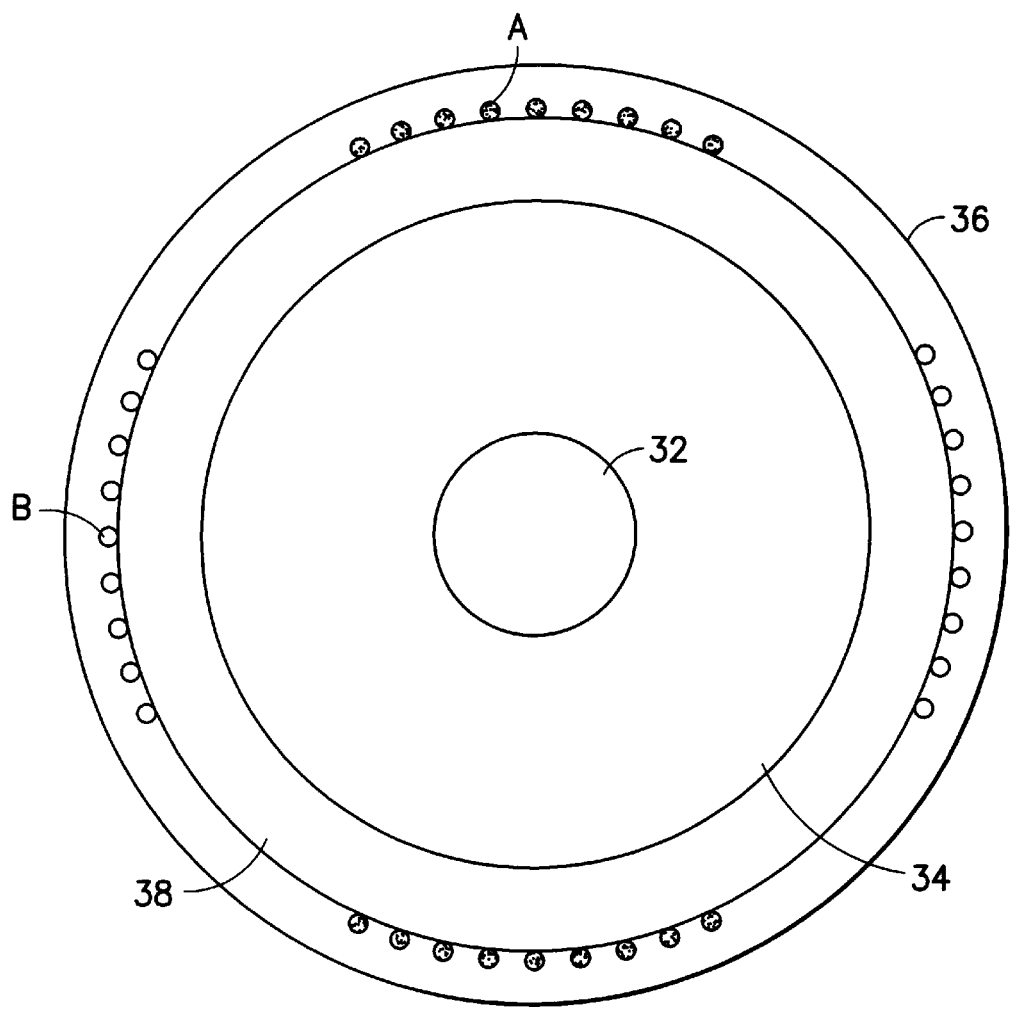
FIG. 2 is a diagram of a cross-section of an embodiment of a logging device for logging while drilling that can be used in practicing embodiments of the invention.

As noted in the referenced copending U.S. patent application Ser. No. 08/936,892, the deep NMR gradient logging apparatus can be utilized in a logging-while drilling application. FIG. 2 illustrates a cross section of an NMR logging device 30 in the form of a logging-while-drilling tool. The tool 30 includes a mud channel 32 for carrying the borehole fluid through the drill string and a drill collar 34 which has a reduced outer diameter at the section shown. The orthogonal coils A and B are wound on a magnetically permeable, laminated core 38 made of a suitable material such as ferrite, laminated permealloy, or tape wound metglass. The protective cover is shown at 36.

Figure 3A:
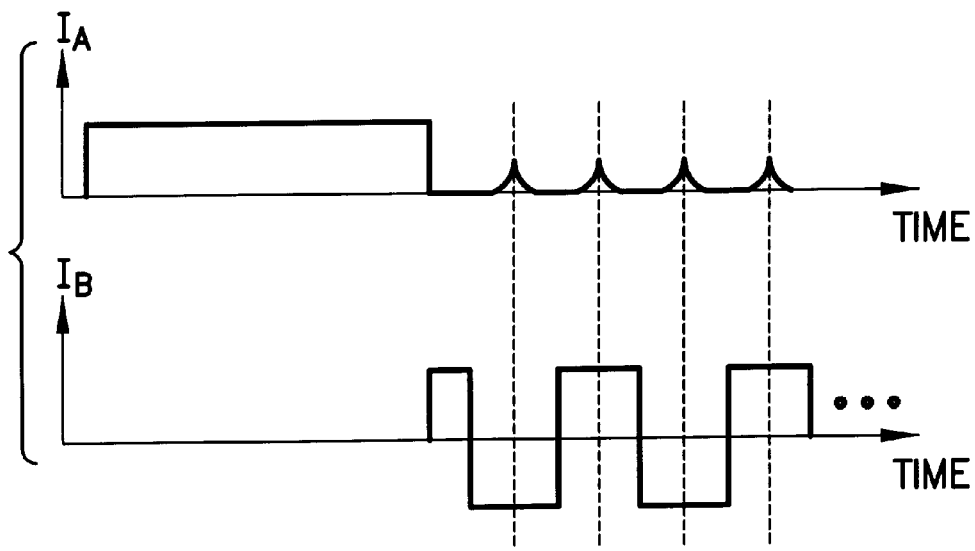
FIGS. 3A and 3B, shows pulse sequences of the type used to obtain spin echoes in pulsed gradient logging as is disclosed in the referenced copending U.S. patent application Ser. No. 08/936,892.
Figure 3B:
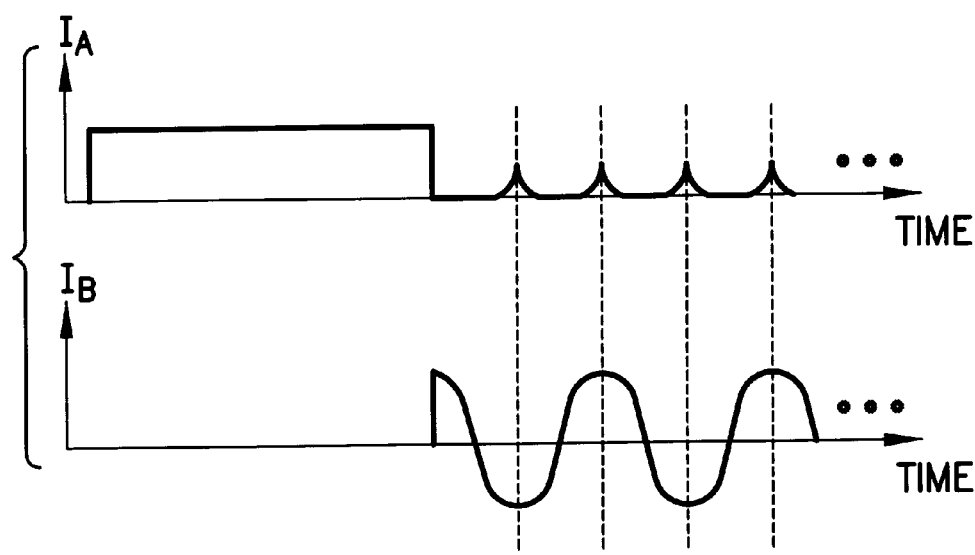

FIGS. 3A and 3B illustrate types of signals and spin echoes that are utilized in the above referenced copending U.S. patent application Ser. No. 08/936,892. Coil A is used to generate a static magnetic field that polarizes the spin magnetization. The spin magnetization is polarized by applying a direct current to the coil A for a period of time approximately equal to or greater than the longitudinal relaxation time, $T_1$, of the formation, thereby aligning the spins along the magnetic field from coil A, namely, $B_0$. The technique of the copending U.S. Patent Application Serial No. refocuses the magnetic moment of protons (spins) in the highly inhomogeneous field $B_0$ by reversing the direction of precession. Following polarization, coil A is turned off and coil B, driven by either commutated direct current (FIG. 3A) or low frequency alternating current (FIG. 3B) is turned on, and produces a magnetic field $B_1$. The spins initially aligned with $B_0$ start precessing in the plane that is perpendicular to $B_1$ at a precession frequency that is proportional to the strength of $B_1$. Reversing the direction of precession brings the spins to the phase at which they started precession, thus generating a gradient-echo, which is shown as being detected in coil A. The free induction decay (FID) signal arising from the volume of investigation in the formation decays rapidly due to the inhomogeneous field. In the preferred embodiment of the technique set forth in the referenced copending Application, the gradient echoes are measured and the FID is not measured. As noted above, the gradient-echoes are detected using coil A.

Figure 4:
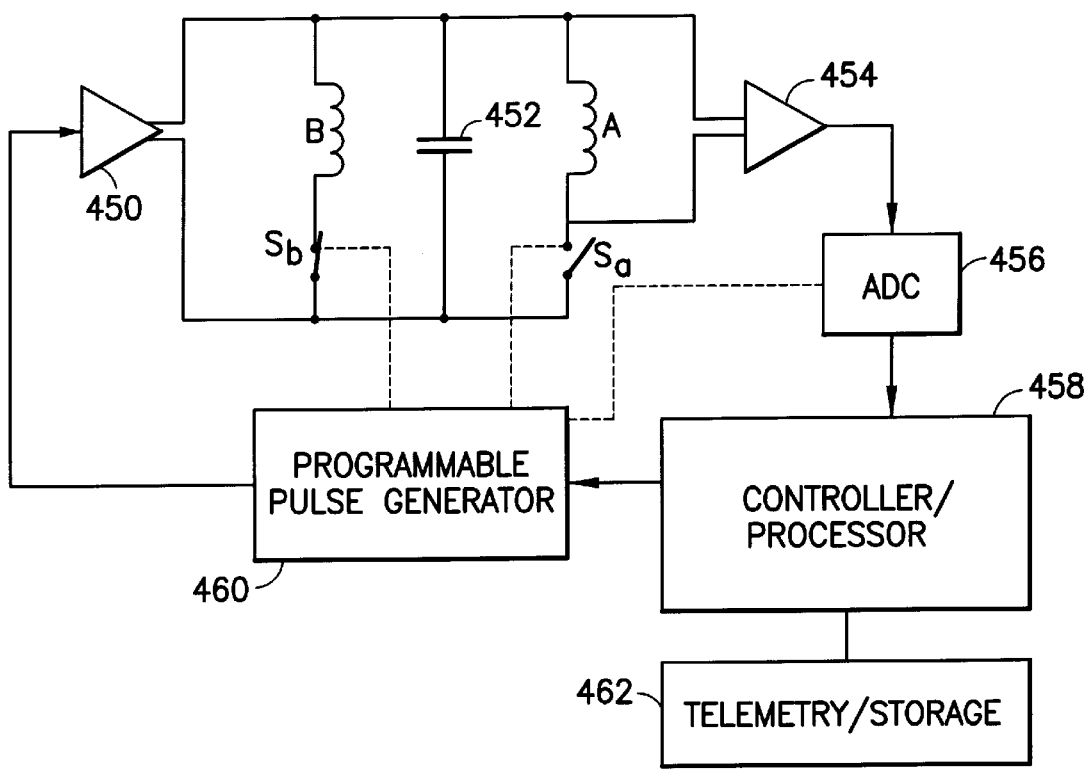
FIG. 4 is a block diagram of a type of circuitry that is utilized in an embodiment of the apparatus set forth in the referenced copending Application, and which can be used in practicing embodiments of the present invention.

FIG. 4 shows a type of circuitry utilized in the above referenced copending U.S. patent application Ser. No. 08/936,892 to implement pulsed gradient logging with a coil arrangement of the type shown in FIG. 1. The output of a current source 450 is coupled to coils A and B. Electronic switches $S_a$ and $S_b$ are respectively coupled in series with coils A and B, and capacitor 452 is coupled across the switch-coil combinations. The output of coil A is coupled to a receiving section that includes an amplifier 454 and an analog-to-digital converter 456. The output of the analog-to-digital converter 456 is coupled to a downhole controller/processor 458, which can be provided with the usual associated memory, timing, integer or floating point processor, and input/output circuitry (not separately shown). An output of the controller 458 is coupled to a programmable pulse generator 460 which, in turn, is coupled to the input of the current source 450. The controller/processor and programmable pulse generator also control the switches $S_a$, $S_b$ and enable the receiving section. Telemetry/storage circuitry 462 is conventionally provided for communicating with the earth's surface. As described in the referenced copending Application, there are three modes of operation: polarization, switch-over, and measurement. The polarization phase has a duration of approximately 0.01 to 8 seconds, based on the formation and the composition of the fluid in the rock pores. During the polarization phase, the nuclear spins in the formation are brought to their thermal equilibrium state in the magnetic field of coil A. Current source 450 drives direct current through coil A. Switch $S_a$ is closed and switch $S_b$ is open. These switches are controlled by the programmable pulse generator 460 and the controller 458. The amplifier 454, analog-to-digital converter 456, and coil B are inactive. At steady state, the capacitor 452 is charged up and current through the capacitor 452 ceases to flow. The entire current output of the current source 450 flows through coil A. The amplifier 454 includes a DC blocking capacitor and a limiter to protect the amplifier from the large voltage on coil A during the polarization and switch-over phases. Once the polarization phase ends, the switch-over phase begins with turning off the current source 450. Coil A and capacitor 452 form a resonator wherein the current in coil A is supplied by capacitor 452. When the current through coil A becomes zero, switch $S_a$ opens and switch $S_b$ closes, thereby switching coil A with coil B in the resonator with minimal loss of energy. Now, the current source 450 drives the resonator formed by coil B and capacitor 452 at its resonance frequency. The current source 450 can output either commutated direct current or low frequency alternating current at the resonant frequency. In either case, the current through coil B is alternating. The period of this alternating current determines the inter-echo time, $T_E$. The successive reversals of the magnetic field of coil B repeatedly refocus the phases of precessing spins thereby forming a sequence of equally spaced gradient-echoes. The period and the inter-echo time are preferably equal and approximately 1 msec.

As is further described in the referenced copending U.S. patent application Ser. No. 08/936,892, the frequency of the detected signal can be mapped to radial position in the formation to obtain an image of the formation, and reference can be made to said copending Application for further details of this feature.

Figure 5:
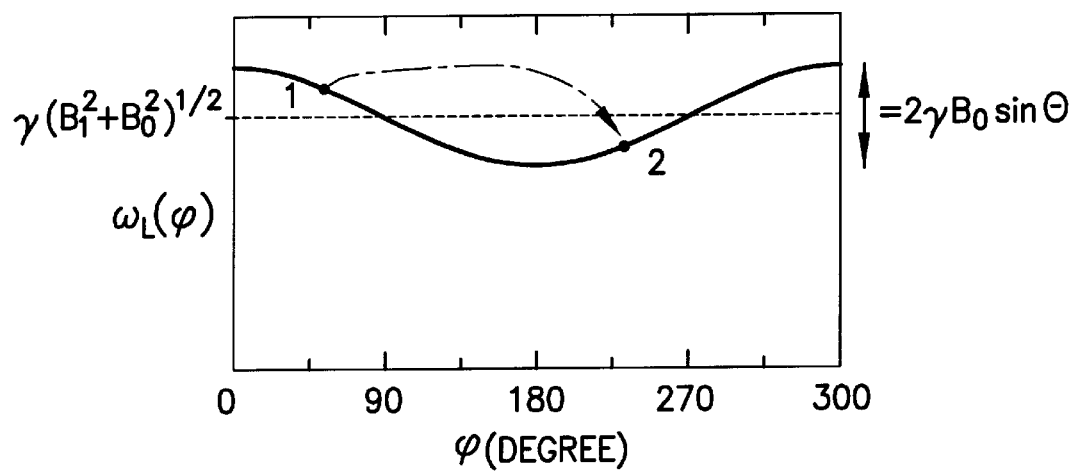
FIG. 5 is a diagram that shows the dependence of local Larmor frequency on the angle between the magnetic field produced by a coil B and the component of the static field that is perpendicular to a coil A, and which is useful in understanding the cause of imperfect refocusing due to a background magnetic field such as earth's magnetic field.

The degree of refocusing with the pulse sequence of FIGS. 3A, 3B is affected by the presence of background fields, such as earth's magnetic field. To demonstrate this, choose at any given point in the formation a local coordinate system such that the $\hat{z}$ axis coincides with the tool axis and the $\hat{x}$ axis with the direction of the field produced by coil B: $B_1 = B_1 \hat{x}$. An arbitrary background field can then be written as $B_e = B_e(\sin\theta\cos\phi\hat{x} + \sin\theta\sin\phi\hat{y} + \cos\theta\hat{z})$. The Larmor frequency at each point is proportional to the magnitude of the total field, $|B_1 + B_e|$ and is given by:

$$\omega_L(\phi) = \gamma\sqrt{B_1^2 + B_e^2}\left[1 + \frac{2B_1 B_e \sin\theta}{B_1^2 + B_e^2}\cos\phi\right]^{1/2} \quad (1)$$

where $\gamma$ is the gyromagnetic ratio. This is plotted in FIG. 5. When the current in coil B is reversed, the angle $\phi$ changes by 180°. If the Larmor frequency with positive current $+I_B$ in the coil is given by point "1" in FIG. 5, then the Larmor frequency with negative current $-I_B$ is shown as point "2" and is, in general, different from point "1".

Depending on the starting angle $\phi$, each successive echo of the echo train of a pulse sequence forms incrementally a little earlier or later than in the absence of a background field. This will lead to a rapid decrease in echo amplitude, even in the absence of any relaxation or diffusion process.

The decay time can be estimated as follows. Assume that the fields of the coils can be approximated as a two-dimensional dipole field, and that the background field is uniform (e.g. earth's magnetic field). In a concentric shell around the tool, the amplitude $B_1$ is constant, but the angle $\phi$ is evenly distributed between 0° and 360°. At a nominal echo at time t, the background field causes an extra uncompensated phase shift of $\Delta\alpha(t) \approx \gamma B_e t \sin\theta\cos\phi$. For each shell, this leads to $((\Delta\alpha(t))^2)_\phi \approx \frac{1}{2}\gamma^2 B_e^2 t^2 \sin^2\theta$. The echo amplitude decays like $\exp\{-\frac{1}{2}((\Delta\alpha(t))^2)\}$, leading to a 1/e decay time $T'_2$ of $$T'_2 = \frac{2}{\gamma B_e \sin\theta}. \quad (2)$$

It can be noted that this decay time is independent of the applied field strength, $B_1$ (in the limit $B_1 >> B_e$). Therefore, the signal from every shell will decay with the same time constant. For the earth magnetic field, $2/\gamma B_e \approx 0.15$ ms, the lower limit for $T'_2$ when the earth's field is perpendicular to the tool axis. Unless the earth's field is exactly aligned with the tool axis, Equation (2) shows that the background field causes a very fast decay of the signal. The pulse sequences hereof reduce or eliminate this decay.

[It can be noted that there is an additional decay when the background field becomes comparable to the applied field beyond a certain depth. This decay is not eliminated with the pulse sequences hereof. The cause of this decay is that the effective field before and after the non-adiabatic reversal are not exactly antiparallel. This means that some of the transverse magnetization will become longitudinal magnetization and not contribute any more to the subsequent echoes. Unlike the dephasing process discussed above, this decay process is only important when the size of the background field becomes comparable to the applied field. The echo attenuation depends on the detail of the pulse sequence, but it is of the order of $1 - (B_e \cos\theta/B_1)^2$ per echo.]

Pulse sequences of embodiments of the invention do not suffer from the rapid dephasing discussed above. With these new pulse sequences, the echo refocuses even in the presence of a static background field, either uniform or non-uniform.

The new pulse sequences hereof consist of combinations of adiabatic and non-adiabatic (sudden) changes of the magnetic field. The non-adiabatic field reversals are already used in the original pulse sequence of FIGS. 3A, 3B above, and are essential to the formation of echoes. The new features, the additional adiabatic rotations before and after the non-adiabatic reversal, are used to average out the angular dependence of the Larmor frequency, shown in FIG. 5. Desirable pulse sequences with these features can be constructed in various ways, e.g. the rotations can be performed about different axes with different angles.

Figure 6:
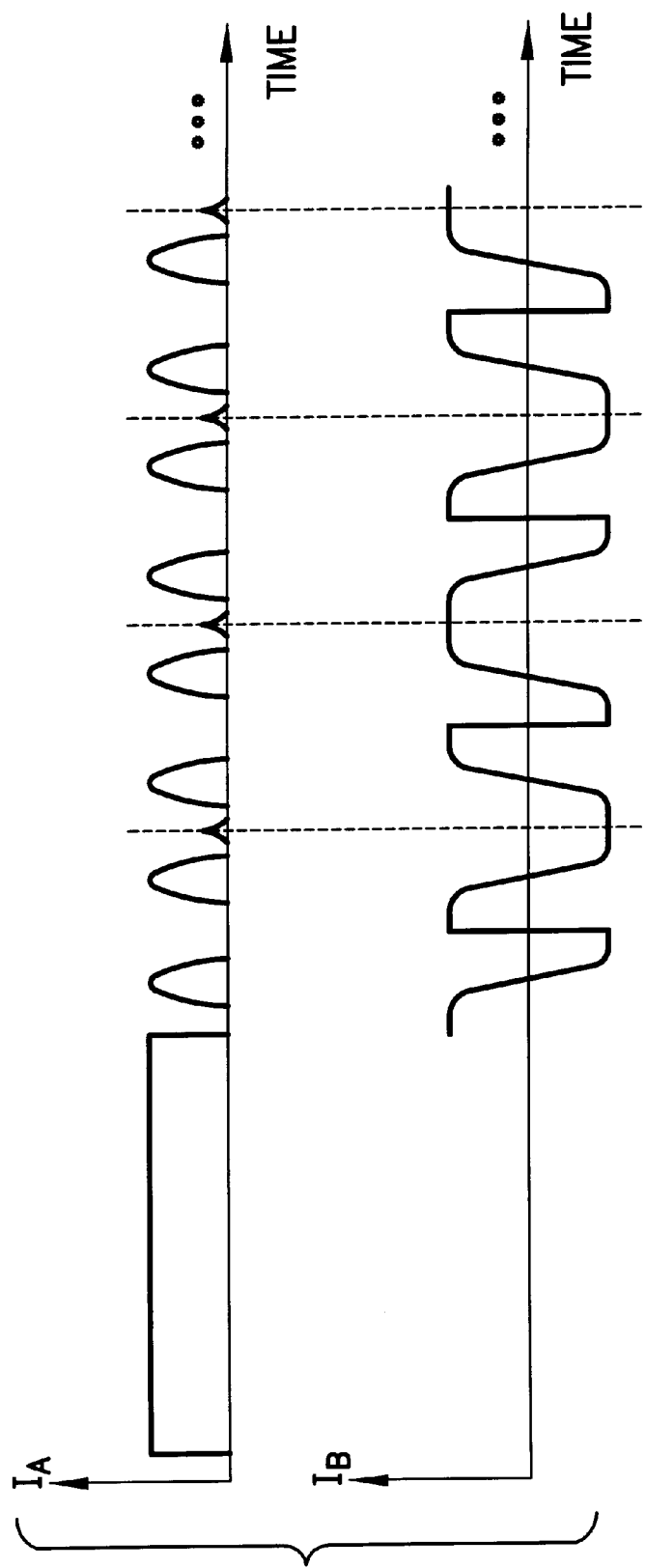
FIG. 6 illustrates signals that can be applied to coils A and B to obtain a pulse sequence in accordance with an embodiment of the invention, and in which adiabatically rotated pulses are used.

An embodiment of the new pulse sequence is shown in FIG. 6. As before, the spins are polarized by the field produced by coil A, which is then switched non-adiabatically to coil B. Next, the direction of the field is turned adiabatically by 180° degrees at every point in the formation (as long as $B_1 >> B_e$), by energizing the coils A and B with currents that have approximately a sin t and cos t dependence, respectively. Then, the field is switched non-adiabatically by 180° as in the original pulse sequence. [In this and subsequent diagrams, the non-adiabatic field reversals are shown in bold line.] Afterwards, the field is again rotated adiabatically by 180°. This leads to an echo (shown centered on the vertical dashed line) that is detected with coil A. Subsequent echoes are generated by repeated application of the refocusing cycle.

Figure 7:
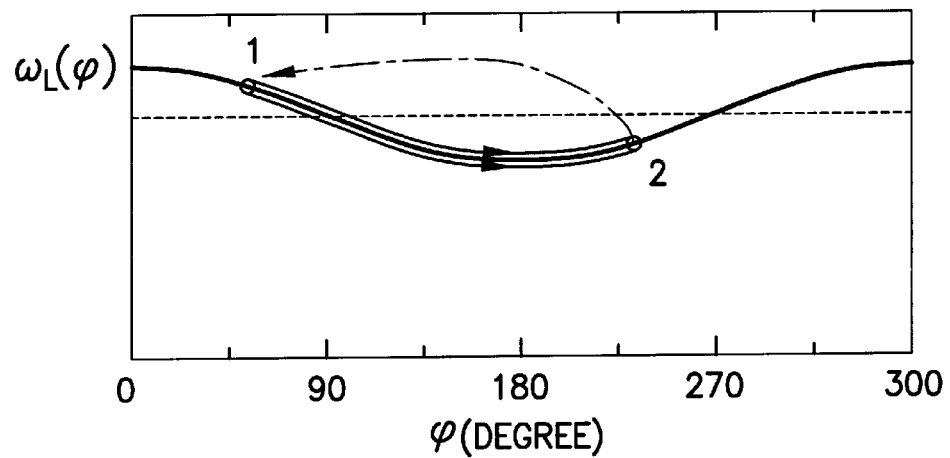
FIG. 7 is a diagram of the type first shown in FIG. 5, and which is useful in understanding how pulse sequences in accordance with embodiments of the invention can solve the problem of imperfect refocusing.

The key is that before and after the non-adiabatic reversal, the spins do not accumulate phase according to the Larmor frequency associated with a single angle $\phi$ (see FIG. 7), but with the whole range between point 1 and 2. After the non-adiabatic switching, the spins experience exactly the same range of values of Larmor frequency as before. This ensures that the phase accumulated before and after the switching exactly cancel, independent of background field.

The condition for adiabatic change of the field direction is, in general, that the direction has to change slowly compared with the instantaneous Larmor frequency. As noted above, this is expected to typically be in the 10 to 100 kHz range, i.e. the adiabatic change can be in the ms range or even faster. It is not critical that the two coils A and B are matched exactly, as long as the adiabatic condition is fulfilled. However, the current shapes before and after the sudden, non-adiabatic reversal should be identical. A further advantage of this pulse sequence is that it makes the echo formation immune to small dc offset in the driving circuitry.

The sign of the current in coil A between the echoes determines whether the field direction is rotated about +180° or −180°. Present analysis does not indicate whether any particular order is preferable. In the basic sequence shown in FIG. 6, positive currents are shown for all A pulses. Another possibility is to alternate the sign of the A current pairs after every echo. This might affect the accumulated Berry's phase.

In the pulse sequence shown in FIG. 6, each non-adiabatic field reversal is abrupt. As was discussed above, the abrupt change can be replaced by a more gradual change as long as the reversal is fast compared to the Larmor frequency of the background field. Essentially, the field strength is first reduced without changing the direction significantly. This is followed by the sudden, non-adiabatic reversal. Then, the field strength is increased again to the same magnitude as before. With the finite reversal time, there are now additional phase shifts associated with the period of field reduction and increase before and after the sudden reversal. In general, they do not cancel exactly, for the same reason as before: the Larmor frequency is not identical for positive and negative currents in the coil when a background field (e.g. earth's magnetic field) is present. For the sequence shown in FIG. 6, these residual phase shifts accumulate and will lead to an extra echo decay, similar to the situation in the original pulse sequence. This problem is solved with the two pulse sequences shown in the embodiments of FIGS. 8 and 9. In these sequences, the residual phase shifts have alternating signs and do not accumulate. Every second echo is unaffected.

The sequence of FIG. 8 consists of two different subcycles. The first subcycle is identical to the one shown in FIG. 6, except that the finite duration of the non-adiabatic inversion has been made explicit. This subcycle consists of an adiabatic 180° rotation, a non-adiabatic 180° rotation, followed by an other adiabatic 180° rotation. In order to cancel the residual phase shift due to the finite duration of the non-adiabatic 180° rotation, the first subcycle is followed by the second subcycle that consists of an adiabatic 360° rotation, a non-adiabatic 180° rotation, followed by another adiabatic 360° rotation.

The second sequence shown in FIG. 9 has only a single subcycle. It consists of an adiabatic 90° rotation, a non-adiabatic 180° rotation, followed by an other adiabatic 90° rotation. A single subcycle does not refocus the echo completely, even in the limit of abrupt non-adiabatic 180° rotation. However, two subcycles in series will compensate the accumulated phase shifts, both for zero and finite reversal times.

In both of the sequences (FIGS. 8 and 9), the duration of the non-adiabatic 180° reversals should be as short as possible, while the duration of the adiabatic rotations should be sufficiently slow. Spins closest to the borehole, experiencing the largest Larmor frequencies, are hardest to reverse non-adiabatically. This is a feature that could be exploited to attenuate the signal from close to the tool.

The pulse sequence shown in FIG. 9 is an example of a more general pulse sequence. In general, a compensated pulse sequence can be constructed from repeated applications of cycles of the following form:

$$C = A_{180°/2n} - S_{180°} - A_{180°/2n} \quad (3)$$

where $A_\alpha$ indicates that the direction of the applied field direction is rotated adiabatically through an angle $\alpha$, and $S_{180°}$ indicates a sudden reversal of the applied field direction.

Figure 10A:
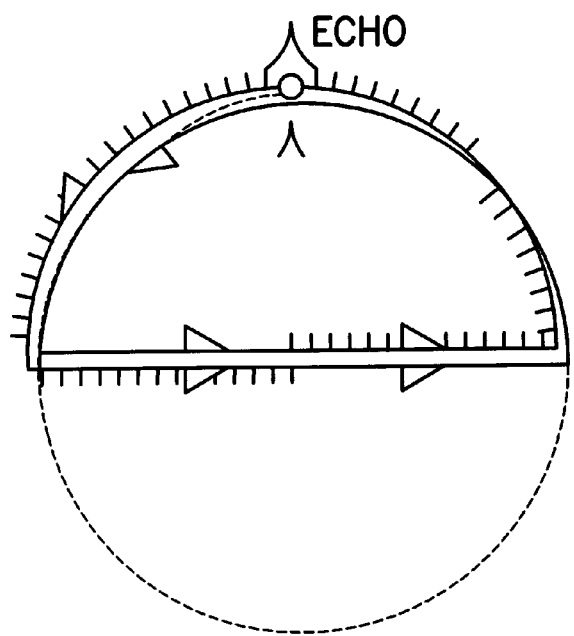
FIGS. 10A and 10B, shows how the angle between the applied field and the background field varies with time, how the phase accumulates (hatched lines or unhatched lines), and where echoes form, using pulse sequence in accordance with an embodiment of the invention. The first 2n−1 echoes are not perfectly refocused in the presence of the background field, the 2nth echo being perfectly refocused.
Figure 10B:
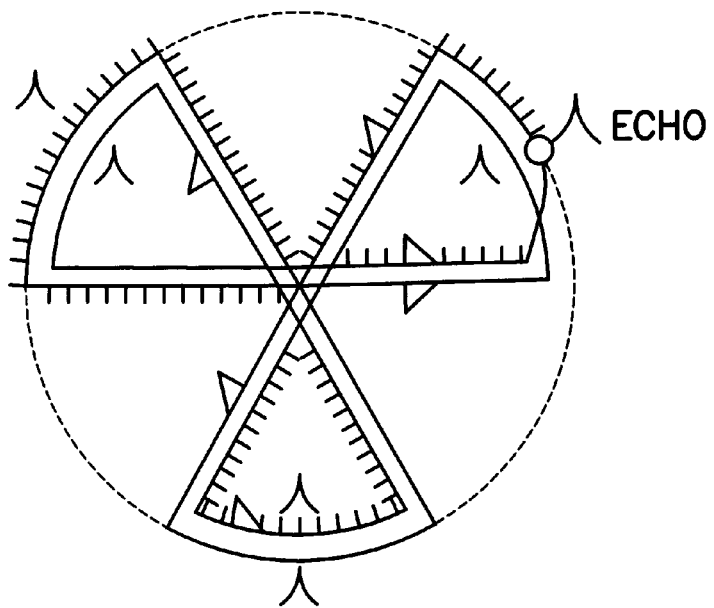

A single cycle C will form an echo in the absence of any background field, but will only refocus imperfectly in the presence of a background field. However, after 2n cycles, the echo will refocus completely, even in the absence of background fields. These properties can be understood with the help of the diagrams shown in FIGS. 10A and 10B. These Figures show the trajectory that the angle $\phi$ (angle between the applied field and the component of the background field orthogonal to the tool axis) undergoes during the pulse sequence. The circle indicates the starting position. After every sudden reversal, the sign of the phase accumulation changes. This is indicated in the Figure by a change from hatching to an absence of hatching. After 2n cycles, the angle $\phi$ is again at the starting position, and all the paths have been traveled twice with opposite sign—resulting in no net phase accumulation and a perfect echo formation. There will be one perfect echo and 2n−1 minor echoes.

For even values of n, it might be advantageous to reverse the direction of rotation after every 2n cycles. Using diagrams such as shown in FIG. 10, it will be understood that many new pulse sequences could be constructed from a combination of cycles with different values and/or signs of n.

Figure 11:
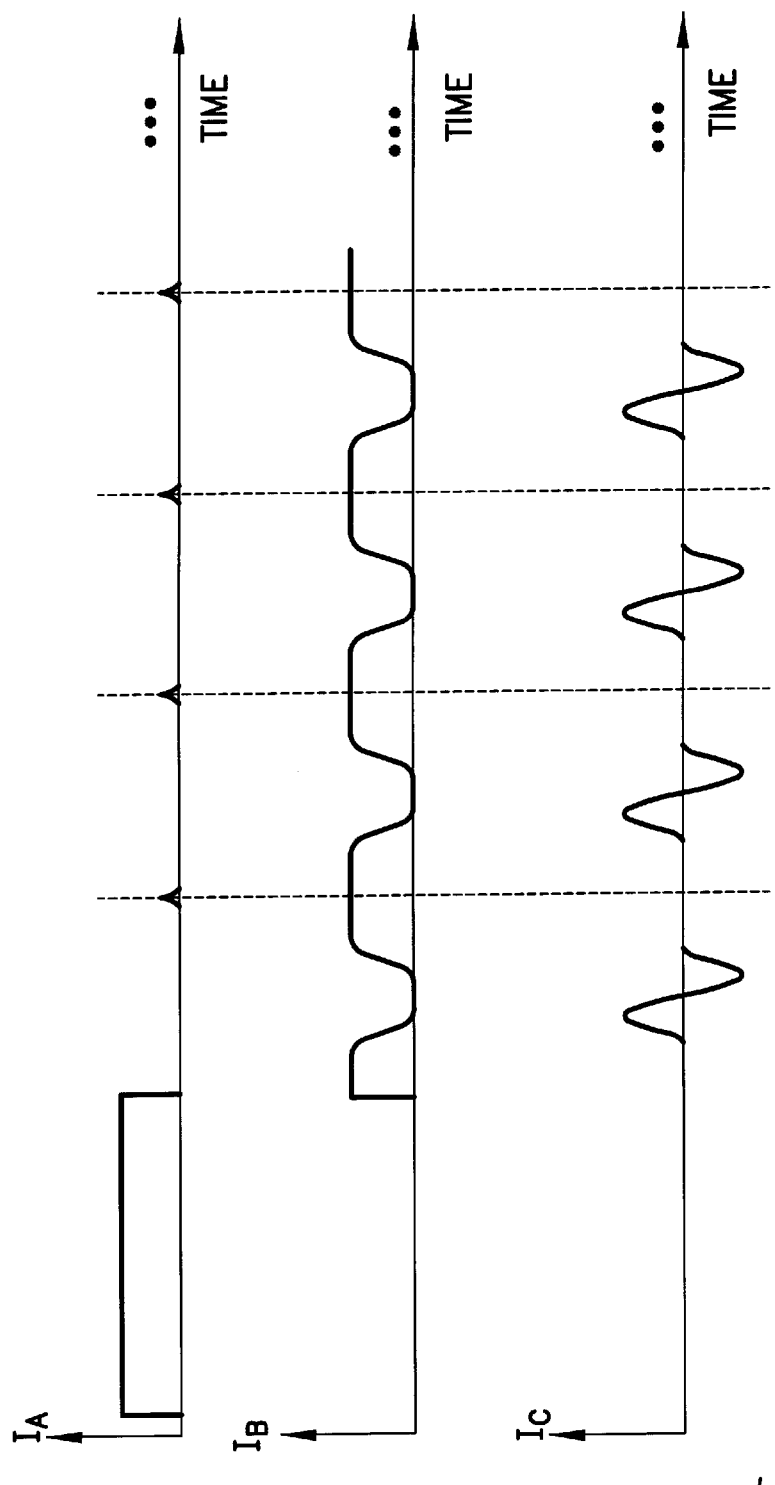
FIG. 11 illustrates signals that can be applied to the coils A, B, and C as a variation of the FIG. 9 approach to obtain a pulse sequence which compensates at every even echo the residual phase shift caused by finite duration of the non-adiabatic field reversal.

A complication of the pulse sequences hereof, as described so far, is that between echoes, current is applied to the same coil as is used to detect the echoes. Note however that the applied current and the detected signal occur at different frequencies. In addition, when extra time intervals with constant currents in the B coil are inserted in the pulse sequence (as shown in FIG. 6 and FIG. 8), the echoes form when no current is applied in the detecting coil. A further approach involves the use of a third coil, C (e.g. in FIG. 1), that is orthogonal to both coil A and coil B. In this case, coil A can still be used to polarize the spins, but afterward, coil C can be used (in conjunction with coil B), instead of coil A, to refocus the echoes. The echoes will still be detected with coil A, but in such case no currents will be applied any more after the polarization period (as was the case in the pulse sequences of FIGS. 3A and 3B). An example of this approach, as a modification of the pulse sequence of FIG. 9, is shown in FIG. 11, wherein coil A is used for prepolarization and echo detection (as in FIG. 9), but not for generation of the sinusoidal component, which is now implemented in coil C. In the circuit of FIG. 4, coil C can be appropriately controlled in a manner similar to that shown for coils A and B.

What is claimed is:

1. A method for determining a nuclear magnetic resonance characteristic of formations surrounding an earth borehole, comprising the steps of:

providing a logging device that is moveable through the borehole;

providing, on said logging device, first and second coils having respective axes that are generally orthogonal;

producing, at said logging device, a prepolarizing signal;

applying pulse sequence signals to said first and second coils;

said pulse sequence signals implementing repeated refocusing of spins in the formations by both adiabatic and non-adiabatic reorienting of said spins to form spin echoes; and detecting, at said logging device, said spin echoes from the formations, said spin echoes being indicative of said nuclear magnetic resonance characteristic of the formations.

2. The method as defined by claim 1, wherein said adiabatic reorientations are performed by varying simultaneously the signals in said first and second coils.

3. The method as defined by claim 2, wherein signals applied to said first and second coils during said adiabatic reorientations are sinusoidal signals.

4. The method as defined by claim 1, wherein a background magnetic field introduces a spurious phase component to said spins during said non-adiabatic reorientations, and wherein said adiabatic reorientations are operative to rotate said spins over a range of angles such that said background magnetic field introduces a further phase component to said spins, said further phase component substantially canceling said spurious phase component.

5. The method as defined by claim 2, wherein a background magnetic field introduces a spurious phase component to said spins during said non-adiabatic reorientations, and wherein said adiabatic reorientations are operative to rotate said spins over a range of angles such that said background magnetic field introduces a further phase component to said spins, said further phase component substantially canceling said spurious phase component.

6. The method as defined by claim 3, wherein a background magnetic field introduces a spurious phase component to said spins during said non-adiabatic reorientations, and wherein said adiabatic reorientations are operative to rotate said spins over a range of angles such that said background magnetic field introduces a further phase component to said spins, said further phase component substantially canceling said spurious phase component.

7. The method as defined by claim 1, wherein the total adiabatic reorientation after each non-adiabatic reorientation is a rotation of 180°+n360°, where n is 0,1,2 . . .

8. The method as defined by claim 2, wherein the total adiabatic reorientation after each non-adiabatic reorientation is a rotation of 180°+n360°, where n is 0,1,2 . . .

9. The method as defined by claim 1, wherein the total adiabatic reorientation before and after each non-adiabatic reorientation is a rotation of 180°+n360°, where n is 0,1,2 . . .

10. The method as defined by claim 2, wherein the total adiabatic reorientation before and after each non-adiabatic reorientation is a rotation of 180°+n360°, where n is 0,1,2 . . .

11. The method as defined by claim 1, wherein the total adiabatic reorientation after each non-adiabatic reorientation is 180°/n, where n is 0,1,2 . . .

12. The method as defined by claim 4, wherein said background magnetic field is earth's magnetic field.

13. The method as defined by claim 7, wherein said background magnetic field is earth's magnetic field.

14. The method as defined by claim 1, wherein said step of producing a prepolarizing signal comprises applying a prepolarizing signal to said first coil.

15. The method as defined by claim 1, wherein said step of detecting spin echoes comprises detecting said spin echoes with said first coil.

16. The method as defined by claim 14, wherein said step of detecting spin echoes comprises detecting said spin echoes with said first coil.

17. The method as defined by claim 5, wherein said step of producing a prepolarizing signal comprises applying a prepolarizing signal to a third coil.

18. The method as defined by claim 17, wherein said step of detecting said spin echoes comprises detecting said spin echoes at said third coil.

19. The method as defined by claim 4, wherein the adiabatic reorientations preceding a pair of successive non-adiabatic reorientations are operative to rotate said spins to have the same polarity before each of said pair of successive non-adiabatic reorientations; whereby dephasing due to the finite transition time of said non-adiabatic reorientations in the background magnetic field is cancelled in the spin echo following the second of said pair of non-adiabatic reorientations.

20. The method as defined by claim 6, wherein the adiabatic reorientations preceding a pair of successive non-adiabatic reorientations are operative to rotate said spins to have the same polarity before each of said pair of successive non-adiabatic reorientations; whereby dephasing due to the finite transition time of said non-adiabatic reorientations in the background magnetic field is cancelled in the spin echo following the second of said pair of non-adiabatic reorientations.

21. The method as defined by claim 12, wherein the adiabatic reorientations preceding a pair of successive non-adiabatic reorientations are operative to rotate said spins to have the same polarity before each of said pair of successive non-adiabatic reorientations; whereby dephasing due to the finite transition time of said non-adiabatic reorientations in the background magnetic field is cancelled in the spin echo following the second of said pair of non-adiabatic reorientations.

22. Apparatus for determining a nuclear magnetic resonance characteristic of formations surrounding an earth borehole, comprising:

a logging device that is moveable through the borehole;

first and second coils on said logging device having respective axes that are generally orthogonal;

means in said logging device for producing a prepolarizing signal;

means for applying pulse sequence signals to said first and second coils, said pulse sequence signals being operative to implement repeated refocusing of spins in the formations by both adiabatic and non-adiabatic reorienting of said spins to form spin echoes; and means for detecting, at said logging device, said spin echoes from the formations, said spin echoes being indicative of said nuclear magnetic resonance characteristic of the formations.

23. Apparatus as defined by claim 22, wherein said adiabatic reorientations are performed by varying simultaneously the signals in said first and second coils.

24. Apparatus as defined by claim 23, wherein signals applied to said first and second coils during said adiabatic reorientations are sinusoidal signals.

25. Apparatus as defined by claim 22, wherein a background magnetic field introduces a spurious phase component to said spins during said non-adiabatic reorientations, and wherein said adiabatic reorientations are operative to rotate said spins over a range of angles such that said background magnetic field introduces a further phase component to said spins, said further phase component substantially canceling said spurious phase component.

26. Apparatus as defined by claim 24, wherein a background magnetic field introduces a spurious phase component to said spins during said non-adiabatic reorientations, and wherein said adiabatic reorientations are operative to rotate said spins over a range of angles such that said background magnetic field introduces a further phase component to said spins, said further phase component substantially canceling said spurious phase component.

27. Apparatus as defined by claim 22, wherein the total adiabatic reorientation after each non-adiabatic reorientation is a rotation of 180°+n360°, where n is 0,1,2 . . .

28. Apparatus as defined by claim 25, wherein said background magnetic field is earth's magnetic field.

29. Apparatus as defined by claim 22, wherein said means for detecting spin echoes comprises means for detecting said spin echoes with said first coil.

30. Apparatus as defined by claim 25, wherein the adiabatic reorientations preceding a pair of successive non-adiabatic reorientations are operative to rotate said spins to have the same polarity before each of said pair of successive non-adiabatic reorientations; whereby dephasing due to the finite transition time of said non-adiabatic reorientations in the background magnetic field is cancelled in the spin echo following the second of said pair of non-adiabatic reorientations.

31. Apparatus as defined by claim 28, wherein the adiabatic reorientations preceding a pair of successive non-adiabatic reorientations are operative to rotate said spins to have the same polarity before each of said pair of successive non-adiabatic reorientations; whereby dephasing due to the finite transition time of said non-adiabatic reorientations in the background magnetic field is cancelled in the spin echo following the second of said pair of non-adiabatic reorientations.

32. Apparatus as defined by claim 22, wherein said means for producing a prepolarizing signal comprises applying a prepolarizing signal to said first coil.

33. A method for determining a nuclear magnetic resonance characteristic of formations surrounding an earth borehole, comprising the steps of:

providing a logging device that is moveable through the borehole;

providing, on said logging device, first and second magnetic field generating sources for generating magnetic fields in the formations that are generally orthogonal;

producing, at said logging device, a prepolarizing signal;

applying pulse sequence signals to said first and second sources;

said pulse sequence signals implementing repeated refocusing of spins in the formations by both adiabatic and non-adiabatic reorienting of said spins to form spin echoes; and detecting, at said logging device, said spin echoes from the formations, said spin echoes being indicative of said nuclear magnetic resonance characteristic of the formations.

34. The method as defined by claim 33, wherein said adiabatic reorientations are performed by varying simultaneously the signals in said first and second sources.

35. The method as defined by claim 34, wherein signals applied to said first and second sources during said adiabatic reorientations are sinusoidal signals.

36. The method as defined by claim 33, wherein a background magnetic field introduces a spurious phase component to said spins during said non-adiabatic reorientations, and wherein said adiabatic reorientations are operative to rotate said spins over a range of angles such that said background magnetic field introduces a further phase component to said spins, said further phase component substantially canceling said spurious phase component.

37. The method as defined by claim 35, wherein a background magnetic field introduces a spurious phase component to said spins during said non-adiabatic reorientations, and wherein said adiabatic reorientations are operative to rotate said spins over a range of angles such that said background magnetic field introduces a further phase component to said spins, said further phase component substantially canceling said spurious phase component.

38. The method as defined by claim 36, wherein said background magnetic field is earth's magnetic field.

39. The method as defined by claim 36, wherein the adiabatic reorientations preceding a pair of successive non-adiabatic reorientations are operative to rotate said spins to have the same polarity before each of said pair of successive non-adiabatic reorientations; whereby dephasing due to the finite transition time of said non-adiabatic reorientations in the background magnetic field is cancelled in the spin echo following the second of said pair of non-adiabatic reorientations.

* * * * *